United States Patent [19]

Greenlee et al.

[11] Patent Number: 5,183,887
[45] Date of Patent: Feb. 2, 1993

[54] SPIROCYCLIC 6-AMIDO-CARBAPENEMS AND AZETIDINONES

[75] Inventors: Mark L. Greenlee, Rahway; Thomas N. Salzmann, No. Plainfield; Frank P. DiNinno, Old Bridge, all of N.J.

[73] Assignee: Merck & Co., Inc., Rahway, N.J.

[21] Appl. No.: 727,192

[22] Filed: Jul. 9, 1991

Related U.S. Application Data

[62] Division of Ser. No. 576,087, Aug. 30, 1990, Pat. No. 5,055,463.

[51] Int. Cl.$^5$ .................... C07D 498/1; C07D 498/2
[52] U.S. Cl. .................................................. 540/364
[58] Field of Search ........................................ 540/364

[56]  References Cited

U.S. PATENT DOCUMENTS 5,104,984  4/1992  Salzmann ........................ 540/200

Primary Examiner—Mark L. Berch
Attorney, Agent, or Firm—Curtis C. Panzer; Raymond M. Speer

[57]  ABSTRACT

New antibacterial spirocyclic 6-amido carbapenems of the structural formulas:

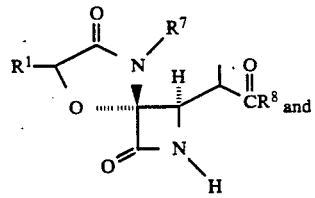

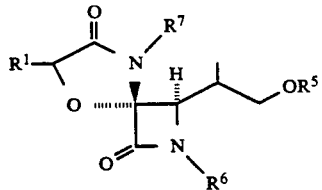

wherein $R^1$ is hydrogen, $C_{1-8}$ substituted or unsubstituted alkyl, or $C_{6-10}$ substituted or unsubstituted aryl; $R^5$ is hydrogen or a protecting group for alcohol; $R^6$ is hydrogen or a protecting group for amido nitrogen; $R^7$ is hydrogen or a protecting group for amido nitrogen; and $R^8$ is hydroxy, hydrogen, $C_{1-8}$ substituted or unsubstituted thioalkyl, $C_{6-10}$ substituted or unsubstituted thioaryl, 5 or 6 membered, substituted or unsubstituted thioheteroaryl; and a process for their synthesis through novel spirocyclic 4-amido azetidinones are disclosed.

11 Claims, No Drawings

SPIROCYCLIC 6-AMIDO-CARBAPENEMS AND AZETIDINONES

This is a division of application Ser. No. 576,087, filed Aug. 30, 1990, now U.S. Pat. No. 5,055,463.

BACKGROUND OF THE INVENTION

1) Field of the Invention

This invention relates to new antibacterial spirocyclic 6-amido-carbapenems and to a process for their synthesis through new intermediates.

2) Brief Description of Disclosures in the Art

Carbapenem antibiotics, particularly imipenem, (see U.S. Pat. Nos. 3,950,377 and 4,194,047) are well known for treating a broad spectrum of gram-negative and gram-positive bacterial infections.

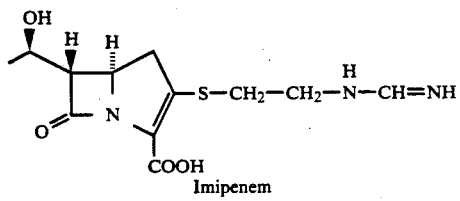

Imipenem

1-$\beta$-Methylcarbapenems, as described in the reference *Heterocycles*, 1984, Vol. 21, pp. 29–40 by D. H. Shih, F. Baker, L. Cama and B. G. Christensen, are extremely useful and effective broad spectrum antibiotics, useful against a wide variety of bacteria including gram-positive bacteria such as *S. aureus, Strep. sp., B. subtilis,* and gram-negative bacteria such as *E. coli, Shigella sp., Enterobacter sp., Klebsiella sp., Proteus, Serratia* and *Pseudomonas sp.*

However, all of the above antibacterial carbapenems utilize 6-substituents other than amido or substituted amido which are the 6-substituents of choice in penicillin, e.g.

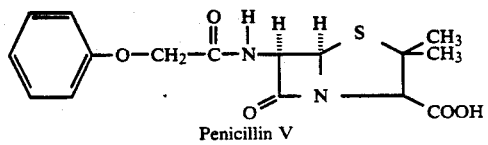

Penicillin V or the cephalosporins, e.g.

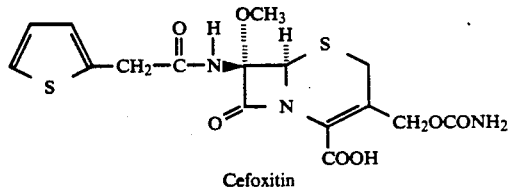

Cefoxitin

6-Amidocarbapenems and penams are known in the art as exemplified in the following references: U.S. Pat. Nos. 4,260,627; 4,206,219; 4,217,343; 4,218,459; 4,218,463; 4,277,482; and 4,298,741 to Merck & Co., Inc. which describe 1-H-6-amidocarbapenems and 1-methyl-6-aminocarbapenems; BE 887,618 and U.S. Pat. No. 4,347,355 to Abbott which describe 1,1-diloweralkyl-6-amidocarbapenems; EPO Publication No. 040,494 and U.S. Pat. No. 4,348,264 to Pfizer which describes 1-hydroxy, acetoxy or 1,1-oxocarbapenems with 6-position conventional penicillin sidechains; EPO Publication Nos. 634,443 and 073,100 and U.S. Pat. No. 4,407,815 to Beecham which describe 1-H-6-amidocarbapenems and penams; Japanese Kokai 58 174 382 to Sanraku-Ocean Co. Ltd. which discloses 6-phthalimido-2-SR carbapenems; and EPO Publication No. 045,198 to Takeda Chem. Ind. Ltd. which discloses 1-alkyl-1-alkoxycarbonyl, cyano or COR-substituted-6-aminocarbapenems.

Literature articles relating to 1-H-6-amidocarbapenems discussing problems in ring closures and ester deblocking reactions include: *Tetrahedron Letters*, 1982, 23 (15), 1545–1548; *Tetrahedron Letters*, 1982, 23 (50), 5339–5342; L. C. Blaszczak, Eli Lilly Co. Report "Joint Great Lakes and Central Regional Meeting", Western Michigan University, May 23–24, 1984; *J. Chem. Soc., Perkins Trans.* I, 1982, 2123–2129; *Helv. Chim. Acta*, 1982, 65, 1378–1384; *J.A.C.S.*, 1982, 104, 4262–4264; *Chem. Pharm. Bull.* 31 2578 (1983); N. Narisada et al. 176th ACS National Meeting, Miami, Fla. 1978.; and *Nouv. J. Chim.* 7 691 (1983).

The assignee herein has been responsible for more recent work with 6-amidocarbapenems. U.S. Ser. No. 213,579, filed Jun. 30, 1988, discloses novel 6-amido-1-methyl-2-(substituted-thio)-carabapenems. Also, U.S. Ser. No. 213,398, filed Jun. 30 1988, discloses novel 6-amido-1-methyl-carbapenems. Further, assignees Ser. No. 727,192 filed Jul. 9, 1991 herewith discloses novel 6-amido-1-methylcarbapenems. Each class of compounds exhibits antibacterial activity.

New antibacterial compounds are constantly being searched for to enhance the potency and decrease the side effects of current existing carbapenem antibiotics. Thus far, spirocyclic 6-amido-carbapenems have not been disclosed in the art.

SUMMARY OF THE INVENTION

It has been found that a new class of compounds, spirocyclic 6-amido-carbapenems exhibit antibacterial activity and can be synthesized from azetidin-2-one starting materials through new intermediates.

By this invention, there is provided a compound of the structural formula:

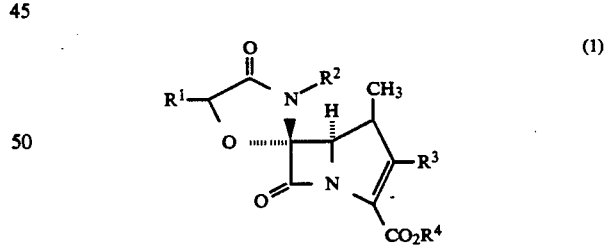

(1)

wherein:

$R^1$ is hydrogen, $C_{1-8}$ substituted or unsubstituted alkyl, or $C_{6-10}$ substituted or unsubstituted aryl;

$R^2$ is hydrogen, $C_{1-8}$ substituted or unsubstituted alkyl, or $C_{2-8}$ substituted or unsubstituted acyl;

$R^3$ is hydrogen, $C_{1-8}$ substituted or unsubstituted thioalkyl, $C_{6-10}$ substituted or unsubstituted thioaryl, or 5 or 6 membered substituted or unsubstituted thioheteroaryl; and $R^4$ is hydrogen, pharmaceutically acceptable alkali metal salt or biolabile ester.

Further provided is a compound of the structural formula:

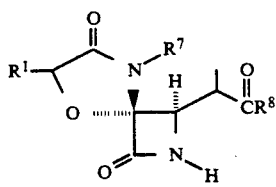
(2)

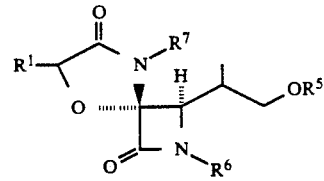
(3)

wherein
- $R^1$ is hydrogen, $C_{1-8}$ substituted or unsubstituted alkyl, or $C_{6-10}$ substituted or unsubstituted aryl;
- $R^7$ is hydrogen or a protecting group for amido nitrogen; and
- $R^8$ is hydroxy, hydrogen, $C_{1-8}$ substituted or unsubstituted thioalkyl, $C_{6-10}$ substituted or unsubstituted thioaryl, 5 or 6 membered, substituted or unsubstituted thioheteroaryl.

Also provided is a compound of the structural formula:

wherein
- $R^5$ is hydrogen or a protecting group for alcohol;
- $R^6$ is hydrogen or a protecting group for amido nitrogen;
- $R^7$ is hydrogen or a protecting group for amido nitrogen; and
- $R^1$ is hydrogen, $C_{1-8}$ substituted or unsubstituted alkyl, or $C_{6-10}$ substituted or unsubstituted aryl;

with the condition that $R^6$ and $R^7$ as protecting groups are separately cleavable.

DETAILED DESCRIPTION OF THE INVENTION

The invention can be readily understood by reference to the following flow sheets which exhibit the processes for the synthesis of the instantly claimed compounds and which exhibit the preferred embodiments.

FLOW SHEET A

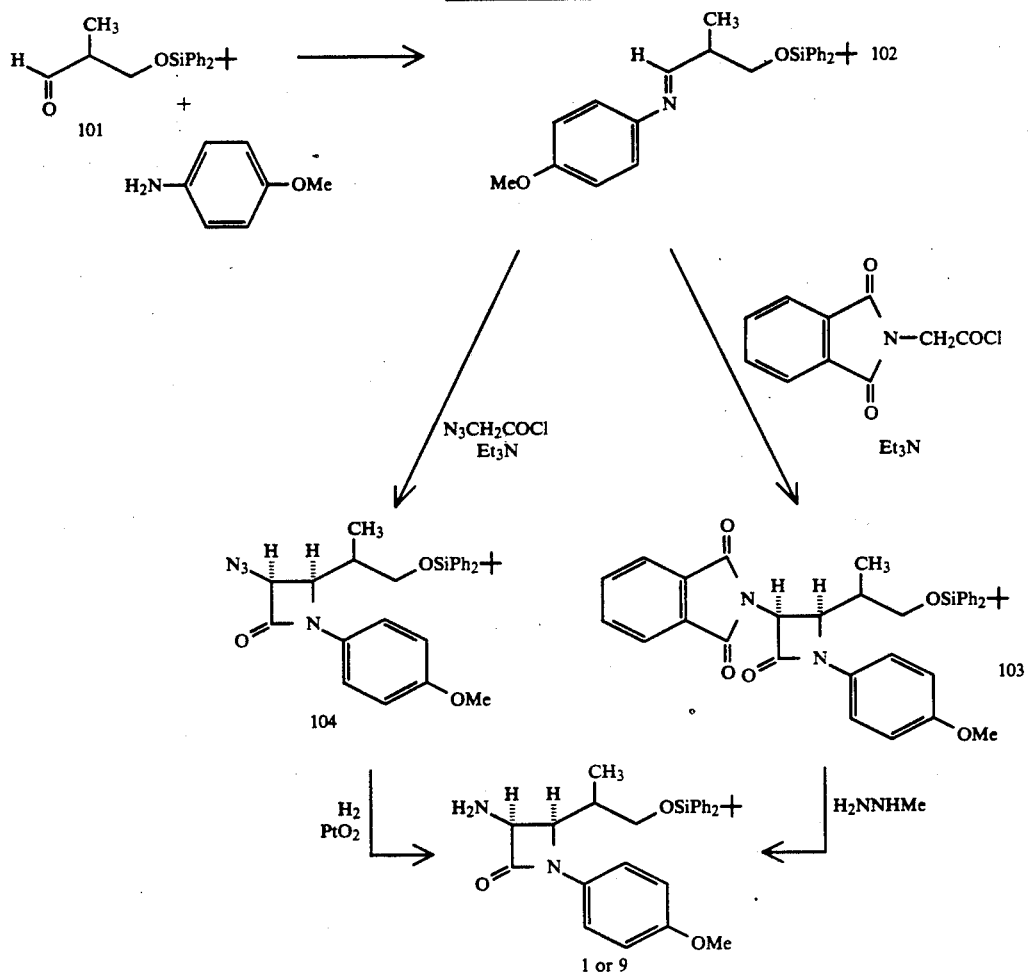

FLOW SHEET B
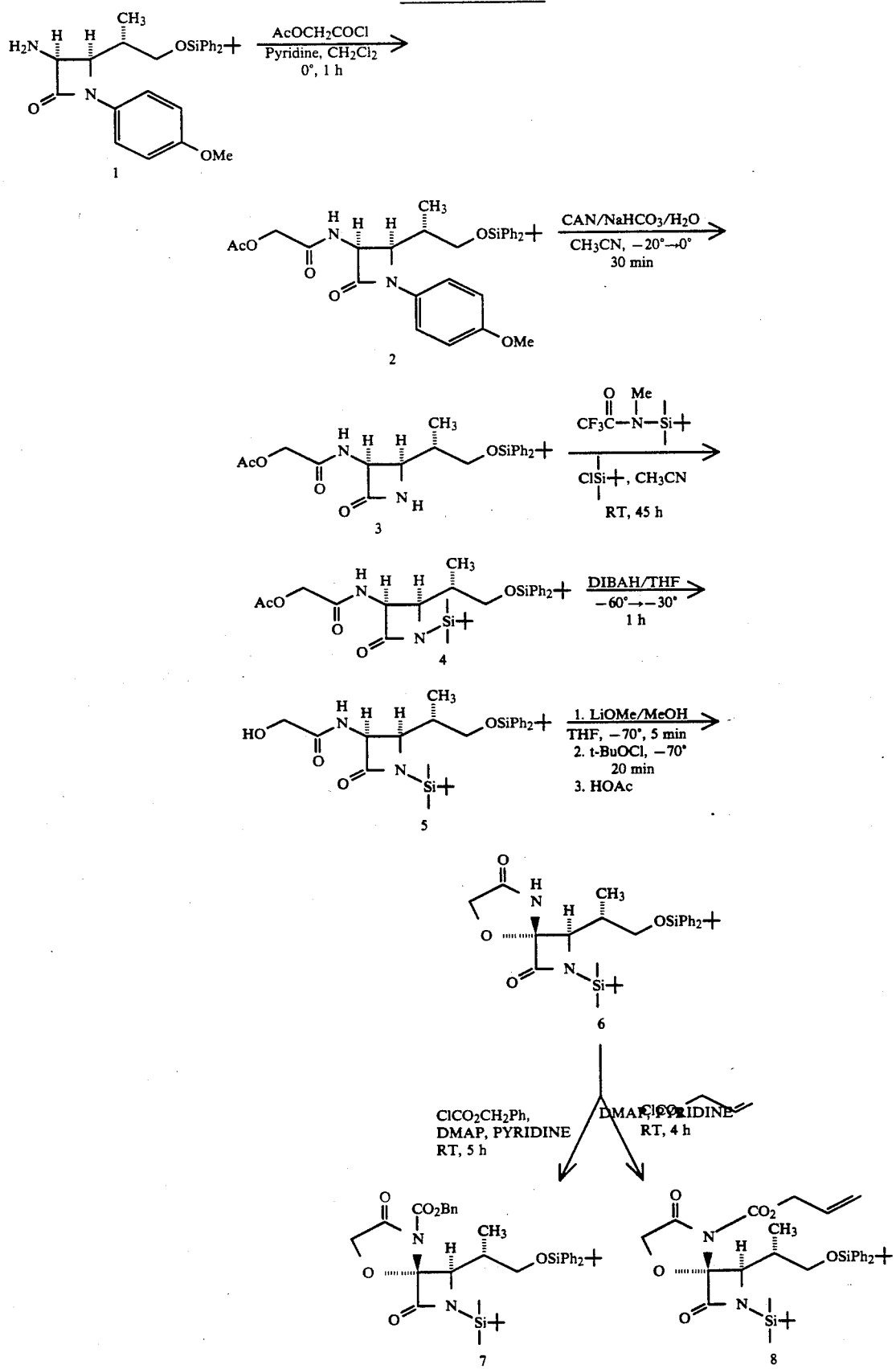

FLOW SHEET C

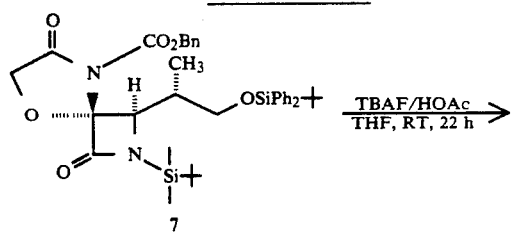
7 — TBAF/HOAc, THF, RT, 22 h →

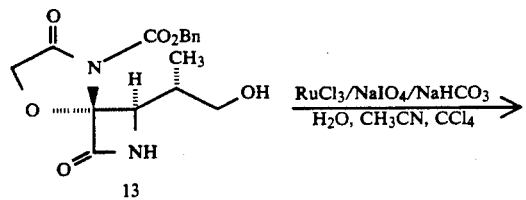
13 — RuCl₃/NaIO₄/NaHCO₃, H₂O, CH₃CN, CCl₄ →

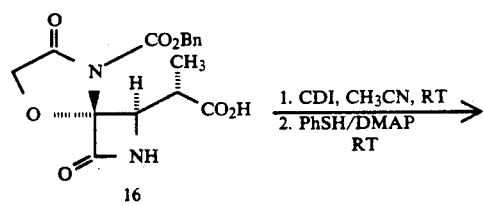
16 — 1. CDI, CH₃CN, RT; 2. PhSH/DMAP, RT →

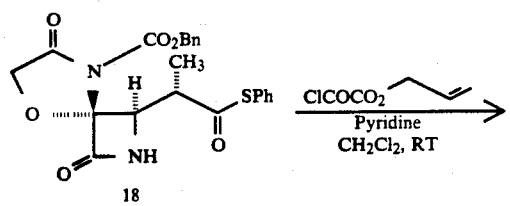
18 — ClCOCO₂(allyl), Pyridine, CH₂Cl₂, RT →

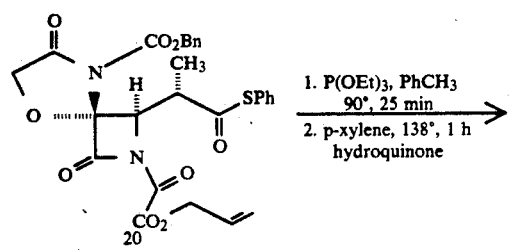
20 — 1. P(OEt)₃, PhCH₃, 90°, 25 min; 2. p-xylene, 138°, 1 h, hydroquinone →

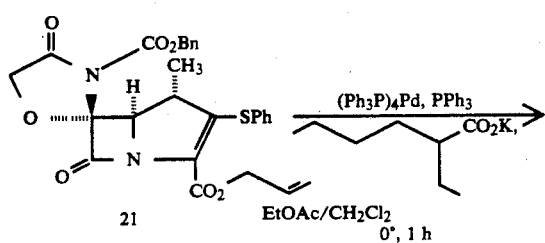
21 — (Ph₃P)₄Pd, PPh₃, 2-ethylhexanoate K, EtOAc/CH₂Cl₂, 0°, 1 h →

-continued
FLOW SHEET C

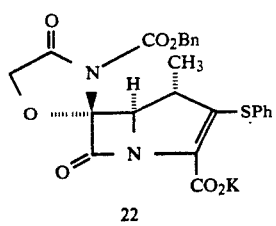
22

FLOW SHEET D

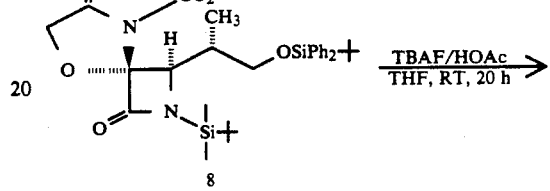
8 — TBAF/HOAc, THF, RT, 20 h →

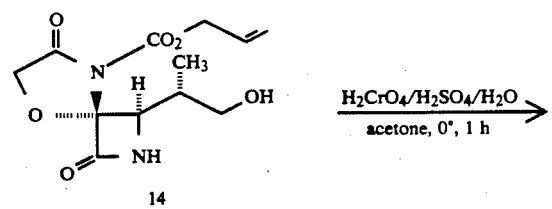
— H₂CrO₄/H₂SO₄/H₂O, acetone, 0°, 1 h →

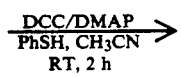
14

— DCC/DMAP, PhSH, CH₃CN, RT, 2 h →

17

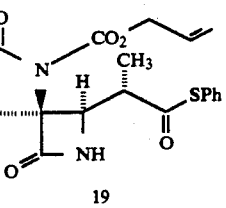
19

FLOW SHEET E

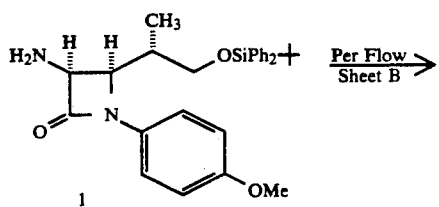
1 — Per Flow Sheet B →

FLOW SHEET E

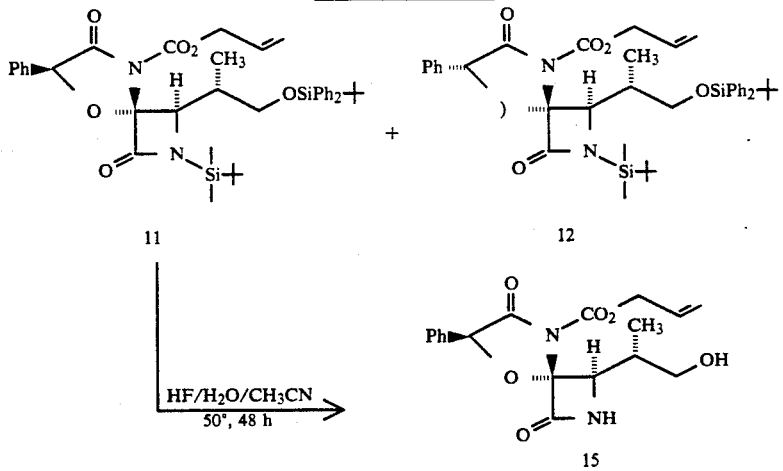

FLOW SHEET F

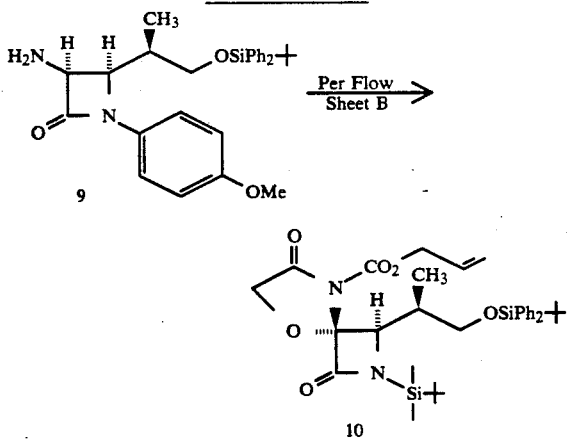

Flow Sheet A illustrates the synthesis of a suitable azetidinone starting material, namely, compounds 1 and 9. Flow Sheets B, E and F exemplify the synthesis of protected intermediates 6,7,8,10,11 and 12 where a heterocyclic ring is formed on the azetidinone and the amido nitrogen and alcohol are protected. Flow Sheet C illustrates the manufacture of end product 22 through functionalized intermediate 18 from protected intermediate 7. Similarly, Flow Sheet D produces functionalized intermediate 19 from protected intermediate 8. Functionalized intermediate 19 may be converted to end products by the steps shown in Flow Sheet C for functionalized intermediate 18. Flow Sheet E produces an intermediate 15 with a substituted heterocyclic ring equivalent to intermediate 14 of Flow Sheet D. Flow Sheet F demonstrates the synthesis of a protected intermediate having a beta-methyl group.

The nomenclature used herein is as follows; the Arabic number refers to a specific compound as designated in the Flow Sheet; a cis or trans designation refers to the 3H, 4H configuration on the azetidinone ring; and the alpha- or beta-methyl designation refers to the orientation of the methyl substituent on the alkyl side-chain at the 4-position of the azetidinone ring, or the 1-methyl substituent on the carbapenem ring system. Thus, in Flow Sheet B, compound 1 demonstrates a cis hydrogen configuration. This same compound also contains an alpha)methyl. Compound 9 demonstrates a beta-methyl.

The compounds of this invention are generally provided as racemic mixtures. The optical isomer depicted in the flow sheets is that which is believed to lead to the greatest antibacterial activity.

Referring to Flow Sheet A, aldehyde 101, 3-(t-butyl-diphenylsilyloxy)-2-methylpropanal, may be made by a three step process. Methallyl alcohol is first protected with a conventional hydroxyl protecting group, e.g. silylation with t-butyldiphenylsilyl chloride at room temperature in the presence of imidazole. Subsequently, the resulting product is hydroxylated by reacting with borane (BH$_3$) at from 0° C. to room temperature in tetrahydrofuran followed in the same step by hydrogen peroxide - sodium hydroxide, also at from 0° C. to room temperature. Finally, the product of the second step is oxidized to the corresponding aldehyde with oxalyl chloride and dimethyl sulfoxide in the presence of triethylamine at from −70° C. to room temperature.

Aldehyde 101 is used to prepare imine 102 by treatment with an amine, such as p-anisidine, and a drying agent such as magnesium sulfate in methylene chloride at room temperature. Other suitable amines which might be employed include benzylamine, p-methoxybenzylamine, 3,4-dimethoxybenzylamine, 2,4-dimethoxybenzylamine, allylamine, and the like.

The imine 102 is subsequently ring closed either to the 3-azidoazetidinones such as compound 104, or to the 3-phthalimidoazetidinones, such as compound 103. In the case of forming compound 103, imine 102 is treated with phthalimidoacetyl chloride and triethylamine in methylene chloride at 0° C. to produce a mixture of compound 103-cis-alpha-methyl and 103-cis-beta-methyl isomers. In the case of forming compound 104, imine 102 is treated with azidoacetyl chloride and triethylamine. This also produces a diastereomeric mixture of isomers as described above.

Either of compounds 103 and 104 can be converted to starting materials 1 and 9. In one instance, a diastereomeric mixture of 1 and 9 can be obtained by the catalytic hydrogenation of compound 104. Alternatively, the isomeric mixture can be obtained by the N-methylhydrazine deacylation of compound 103. The isomeric mixture of 1 and 9 can be separated chromatographically. The synthesis of starting materials 1 and 9 is further described in U.S. Ser. No. 213,579 filed Jun. 30, 1988, and hereby incorporated by reference.

Starting materials 1 and 9 are prepared with a hydroxyl protecting group, included in $R^5$ which specifically is t-butyldiphenylsilyl. Persons skilled in the art will readily recognize that the identity of this protecting group is not critical to the invention, so long as it performs a protecting function through the desired synthesis. Other hydroxyl protecting groups known in the art (see for example T. W. Greene, *Protective Groups in Organic Synthesis*, John Wiley & Sons, Inc., 1981; Chapter 2) which can be used include: t-butyldimethylsilyl, benzyl, p-methoxybenzyl, methoxymethyl, benzyloxycarbonyl, and the like.

Starting materials 1 and 9 are also prepared with an amido nitrogen protecting group, included within $R^6$, on the 1-position of the azetidinone ring. In this instance the amido nitrogen protecting group is 4-methoxyphenyl, which is usefully attached as a protecting group through synthesis of the starting materials 1 and 9 in Flow Sheet A and through certain initial reactions of Flow Sheet B. Subsequently, 4-methoxyphenyl is replaced, as will be discussed, with 6-butyldimethylsilyl as a protecting group. Thus, the selection of a protecting group for the amido nitrogen of the azetidinone ring requires consideration of changing circumstance through the synthesis. This consideration and the selection is within the skill of the art. One circumstance for consideration is that the protecting group for the amido nitrogen of the azetidione ring and the protecting group for the amido nitrogen on the 3-position on the azetidinone ring must be separately formable and cleavable. This characteristic is necessary so that these amido nitrogens can be separately manipulated. Another consideration is that it is convenient, for example in the synthesis of compound 13 that the subject amido nitrogen protecting group for compound 7 is simultaneously cleavable with the hydroxyl protecting group. Preferred as the protecting group for the amido nitrogen of the azetidinone ring are silyl hydrocarbons, particularly such where at least one of the three hydrocarbon substituents has 4 or more carbon atoms. Thus, including t-butyldimethylsilyl, preferred protecting groups are dimethylphenylsilyl or t-butyldiphenylsilyl. Protecting groups in general for amines are taught by T. W. Greene, *Protective Groups in Organic Synthesis*, John Wiley and Sons, Inc., 1981; Chapter 7.

Starting materials 1 and 9 are not prepared with a protecting group on the amido nitrogen on the 3-position of the azetidinone ring. However a protecting group in this position is necessary at some point for later steps in the synthesis to final product. Disclosed and included in $R^7$ is a carbamate protecting group, specifically, benzyl carbamate or allyl carbamate. Other protecting groups may be suitable considering the above comments made in connection with the selection of $R^6$ protecting groups. Suitable protecting groups, in general, for use with the amido nitrogen on the 3-position azetidinone ring are taught as above by T. W. Greene, *Protective Groups in Organic Synthesis*, John Wiley and Sons, Inc., 1981; Chapter 7.

Flow Sheet B synthesizes protected intermediates 7 and 8 from starting material 1. Starting material 1 is acylated with acetoxyacetyl chloride at 0° C. for 1 hour to produce compound 2 as in Example 1. Subsequently, ceric ammonium nitrate is employed to cleave the p-methoxyphenyl protecting group from the amido nitrogen of the azetidinone ring to produce compound 3 while warming the mixture from −20° C. to 0° C. over 30 minutes as in Example 2. This same amido nitrogen is again substituted with a protecting group of t-butyldimethylsilyl to produce compound 4 by reacting with N-(t-butyldimethylsilyl)-N-methyltrifluoroacetamide and t-butyldimethylsilylchloride at room temperature for 45 hours. The identity of this protecting group, included within $R^6$ and as stated above, is not critical but is intended to perform a specific function on the intermediate. In the following step, the acetyl group of compound 4 is removed to deprotect a hydroxy group of compound 5 as in Example 4. With protection of the hydroxy removed, compound 5 has a amido substitution on the 3-azetidinone position that may be cyclized to a spiro-heterocycle. This is accomplished as demonstrated in Example 5 by cooling compound 5° to −70° C. and treating with lithium methoxide, followed in 5 minutes by the addition of t-butylhypochlorite, followed in an additional 15 minutes by glacial acetic acid to produce compound 6. In compound 6, the oxazolidinone amide nitrogen may be protected, as discussed above with a protecting group included within $R^7$. In one instance, this amido nitrogen might be protected as a benzyl carbamate by reacting with benzyl chloroformate to produce compound 7 as shown in Example 6. In another instance, the amido nitrogen might be protected as an allyl carbamate by reacting with allyl chloroformate to produce compound 8 as shown in Example 7. Thus, Flow Sheet B demonstrates the synthesis of protected intermediates 6, 7 and 8. "Protected intermediate" refers herein to those intermediate compounds immediately resulting from formation of the spiroheterocyclic ring on the 3-position of the azetidinone.

Flow Sheet C demonstrates production of end product 22 from protected intermediate 7. As a first step, the silyl protective groups of protected intermediate 7 are simultaneously cleaved to produce compound 13 by reacting with tetra-n-butylammonium fluoride and glacial acetic acid as shown in Example 10. The object, of course, for removal of these protecting groups is to make the necessary substitutions and close a fused 5-membered ring to form the carbapenem. With the protecting group removed, the hydroxyl function of compound 13 is oxidized with sodium metaperiodate - ruthenium trichloride hydrate in the presence of sodium bicarbonate to replace this function with a carboxyl and form compound 16 as shown in Example 13. In the synthesis step following formation of compound 16, $R^8$ is determined, which can conveniently also be $R^3$. Thus, the carboxy of compound 16 can be left in place and the compound converted to a compound 18 analog or compound 16 can be converted to a carbonyl with substitution, $R^8$, that may or may not be the final substitution, $R^3$. In the instance of Flow Sheet C, the carboxy of compound 16 is converted to a thioester, compound 18, by reaction with 1,1′-carbonyldiimidazole followed by 4-dimethylaminopyridine and thiophenol as shown in Example 15. The thiophenol forms $R^8$, thiophenyl, a thioaryl which is also suitable as final substitutent, $R^3$. Otherwise, $R^8$ might be a thioalkyl, such as 2-thio(-cyanoethyl), or thioheteroaryl, such as 2-thiopyridyl, each suitable also as $R^3$. With the $R^8$ substitution on the carbonyl, the amido nitrogen of the azetidinone ring is substituted to form compound 20. This is accomplished by reacting compound 18 with allyl oxalyl chloride at room temperature as demonstrated in Example 23. The ally oxalyl chloride not only provides the necessary substitution to close the fused ring and form the carbapenem but also, in this case, provides for a precursor to —COOR$^4$. The precursor to —COOR$^4$ is a carboxy ester where the ester is a carboxyl protecting group. Other carboxyl protecting groups are known which are suitable to protect this carboxyl during the subsequent reaction to close the fused ring.

To close the fused ring and form the carbapenem, compound 20 was first heated to 90° C. with excess triethylphosphite to form a crude phosphorane which was subsequently heated in refluxing p-xylene in the presence of hydroquinone to complete cyclization in about 1 hour to form compound 21 as demonstrated in Example 24. End product 22 is obtained from compound 21 by deprotecting the carboxyl group of the 6-position on the carbapenem, replacing the protecting group with hydrogen, pharmaceutically acceptable alkali metal salt, or biolabile ester. In the instance of Flow Sheet G, this is accomplished by adding in sequence at 0° C. triphenylphosphine, potassium 2-ethylhexanoate, and tetrakis(triphenylphosphine)palladium as demonstrated in Example 31. Other pharmaceutically acceptable alkali metal salts include sodium. Suitable biolabile esters are metabolizable esters known in the penicillin, cephalosporin and penem arts to be easily cleaved within the body to the parent acid. Examples of such esters are indanyl, phthalidyl, methoxymethyl, glycloxymethyl, phenylglycyloxymethyl, thienylglycyloxymethyl, acetoxymethyl and pivaloyloxymethyl.

Flow Sheet C synthesizes end product 22 with a substitution, R$^2$, on the amido nitrogen at the heterocyclic ring which is the protecting group, R$^7$, employed during the synthesis. Substitution suitable as R$^2$ are those substitutions which will not interfere with the activity of the end product. Clearly, such a definition of R$^2$ will include certain protecting groups for the amido nitrogen, R$^7$. Thus, end product may conveniently have substitution R$^2$ which was utilized in synthesis as an amido nitrogen protecting group. Suitable R$^2$ include hydrogen; C$_{1-8}$ substituted or unsubstituted alkyl, such as, methyl, ethyl, propyl, etc.; or C$_{1-8}$ substituted or unsubstituted acyl, such as, benzyl carboxylate, allyl carboxylate, acetyl, benzoyl, propanoyl, etc.

Flow Sheet D demonstrates how the synthesis might vary where allyl carbamate is chosen as the protecting group for the amido nitrogen on the 3-position azetidinone ring, such as in protected intermediate 8. As with protected intermediate 7, the silyl protective groups of protected intermediate 8 are simultaneously cleaved to produce compound 14 as demonstrated in Example 9. However, producing compound 17, an analog of compound 16, advantageously differs in the case of the allyl carbamate. Compound 14 is cooled to 0° C. in acetone and mixed with excess Jones reagent and allowed to warm to room temperature to produce compound 17 as demonstrated in Example 14. Compound 17 is transformed to compound 19, the analog of compound 18, by mixing at room temperature with 4-dimethylaminopyridine, thiophenol, and dicyclohexylcarbodiimide as demonstrated in Example 16. Compound 19 may be converted to compounds analogous to end product 22 according to the reaction scheme of Flow Sheet C.

Flow Sheet E illustrates the production of a phenyl substituted heterocyclic ring on the 3-position of the azetidinone ring, compound 15, analogous to compound 14. The steps of Flow Sheet B are followed, with one exception, to first produce protected intermediates 11 and 12 which are analogs to protected intermediate 8. Acetylmandelyl chloride is employed in the place of acetoxyacetyl chloride to acylate the amine on the 3-position of the azetidinone as demonstrated in Example 9. Subsequently, protected intermediates 11 and 12 have the silyl protecting groups removed by heating with acetonitrile and hydrofluoric acid to produce compound 15 as demonstrated in Example 12, an analog to compound 14 of Flow Sheet D. Where there is phenyl substitution on the heterocyclic ring as in compound 15, the method of Example 12 is preferred to remove the silyl protecting groups. Compound 15 may be further elaborated to end products by the methods of Flow Sheets C and D.

Flow Sheet F illustrates the synthesis of a protected intermediate 10, having "beta-methyl" substitution on the 4-position of the azetidinone. This synthesis begins with starting material 9 and could follow the path of Flow Sheet B as demonstrated in Example 8. Further synthesis to end product might proceed according to Flow Sheets C and D, producing analogous "beta-methyl" compounds, but it is possible that sterically, the "beta-methyl" could prevent closure of the fused ring to produce the carbapenem. In terms of Flow Sheets C and D, it may be difficult to obtain the beta-methyl analog of compound 21 from the beta-methyl analog of compound 20. Thus, at some point following the production of protected intermediate 10, it may be necessary to epimerize the beta-methyl to alpha-methyl prior to obtaining the beta-methyl analog to compound 20. For example, protected intermediate 10 is reacted according to Flow Sheet D to a beta-methyl compound 14 analog, and further reacted to a beta-methyl compound 17 analog. At this point, the compound 17 analog could be epimerized by first treating with a strong base such as LDA, lithium diisopropylamide, to deprotonate the alpha proton of the propionic acid side chain. Subsequently, this side chain would be reprotonated with an acid such as acetic acid to form a diastereomeric mixture of alpha-methyl and beta-methyl. The alpha-methyl could be separated and converted continue according to Flow Sheets C and D to end product. As an alternative example, the analog to beta-methyl compound 17 could be further converted to the analog of compound 19. This analog could be treated with a base such as triethylamine or a stronger base such as 1,8-diazabicyclo-[5.4.0]-undec-7-ene, DBU, to deprotonate and reprotonate to form again, a mixture of alpha-methyl and beta-methyl. From compound 19, the alpha-methyl isomer, the synthesis could continue according to Flow Sheets C and D.

The novel compounds in the different chemical classes of the present disclosure are believed to be valuable antibiotics active against various Gram-positive and Gram-negative bacteria and accordingly find utility in human and veterinary medicine. Representative pathogens which are sensitive to these antibiotics include: *Staphylococcus aureus*, and *Escherichia coli*. The antibacterials of the invention are not limited to utility as medicaments; they may be used in all manner of industry, for example: additives to animal feed, perservation of food, disinfectants and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage amount is usually the pure compound I in sterile water solution or in the form of a soluble powder intended for solution.

The following examples are illustrative of the invention and should not be construed as being limits on the scope and spirit of the instant invention.

EXAMPLE 1

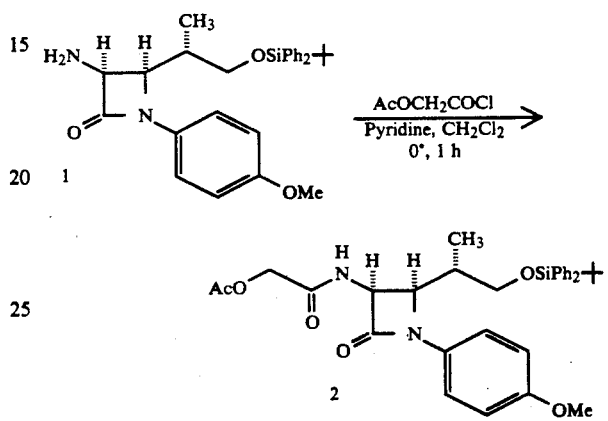

($\pm$)-3S-acetoxyacetamido-4R-(1-t-butyldiphenyl-silyloxy-2S-propyl)-1-p-methoxyphenyl-azetidin-2-one
(2)

To a solution of ($\pm$)-3S-amino-4R-(1-t-butyldiphenylsilyloxy-2S-propyl)-1-p-methoxyphenyl-azetidin-2-one 1 (2.519 g, 5.162 mmol) in 40 ml of methylene chloride at 0° C. were added pyridine (0.67 ml, 8.3 mmol) and acetoxyacetyl chloride (0.72 ml, 6.7 mmol). After 1 hour, the reaction mixture was diluted with ethyl ether and washed successively with sat. NH$_4$Cl, sat. NaHCO$_3$, and brine. Drying (MgSO$_4$) and evaporation yielded 2.919 g (96%) of the title compound as a pale yellow solid which required no purification. $^1$H-NMR (300 MHz, CDCl$_3$): $\delta$ 0.95 (d, J=7.26 Hz, CHCH$_3$), 1.10 (s, Sit-Bu), 2.06 (s, CH$_3$CO$_2$—), 2.0–2.2 (m, CHCH$_3$), 3.55–3.70 (m, CH$_2$OSi), 3.75 (s, OCH$_3$), 4.3–4.5 (m, 3H, H$_4$, CH$_2$OAc), 5.60 (dd, J=9.34, 5.49 Hz, H3), 6.74 (d, J=9.7 Hz, 2H, ArH), 7.2–7.7 (m, 12H, ArH).

IR (CHCl$_3$): 1755 ($\beta$-lactam), 1695 cm$^{-1}$ (amide).
FAB-MS: m/e=589 (M+H).

EXAMPLE 2

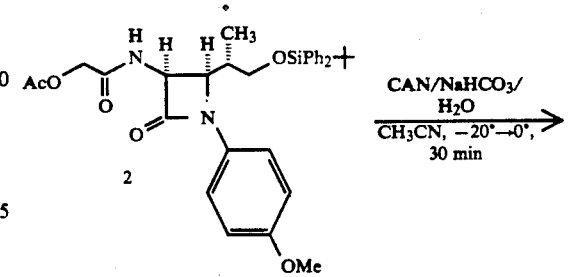

-continued

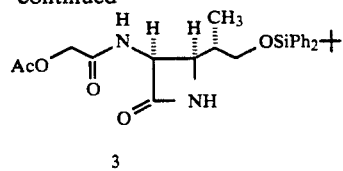

3

(±)-3S-acetoxyacetamido-4R-(1-t-butyldiphenyl-silyloxy-2S-propyl)-azetidin-2-one (3)

To a solution of the azetidinone 2 (2.919 g, 4.964 mmol) in 50 ml of acetonitrile and 25 ml of tetrahydrofuran at −20° C. was added dropwise a solution of ceric ammonium nitrate (8.16 g, 14.9 mmol) in 25 ml of water which had been buffered by the portion-wise addition of sodium bicarbonate (1.25 g, 14.9 mmol). The orange reaction mixture was allowed to warm to 0° C. during 30 minutes and was then diluted with ethyl acetate and washed successively with water, 10% $Na_2SO_3$, sat. $NaHCO_3$, and brine. Drying ($MgSO_4$) and evaporation gave a brown oil which was purified by flash chromatography through 250 g of silica gel (75:25 EtOAc/hexane) to yield 1.630 g (68%) of the title compound as a white solid.

$^1$H-NMR (300 MHZ, $CDCl_3$): δ 0.82 (d, J=6.47 Hz, $CHCH_3$), 1.06 (s, Sit-Bu), 1.60–1.75 (m, $CHCH_3$), 2.14 (s, $CH_3CO_2$—), 3.65 (d, J=4.27 Hz, —$CH_2OSi$), 3.69 (dd, J=4.94, 9.58 Hz, H4), 4.50–4.65 (AB, $CH_2OAc$), 5.39 (dd, J=4.94, 9.58 Hz, H3), 5.81 (bs, NH), 7.15 (d, J=9 Hz, NH), 7.35–7.70 (m, 10H, $SiPh_2$).

IR ($CHCl_3$): 3430 (NH), 1765 (β-lactam), 1695 cm$^{-1}$ (amide).

FAB-MS: m/e=483 (M+H).

EXAMPLE 3

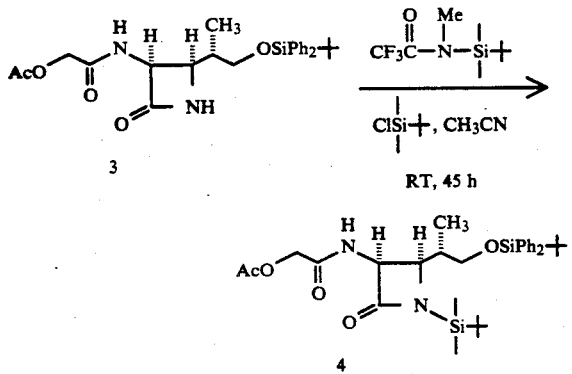

(±)-3S-acetoxyacetamido-1-t-butyldimethylsilyl-4R-(1-t-butyldiphenylsilyloxy-2S-propyl)azetidin-2-one (4)

To a solution of the azetidinone 3 (1.630 g, 3.382 mmol) in 25 ml of acetonitrile were added N-(t-butyldimethylsilyl)-N-methyltrifluoroacetamide (2.0 ml, 8.5 mmol) and t-butyldimethylsilyl chloride (0.050 mg, 0.34 mmol). The solution was stirred at room temperature for 45 hours, and was then evaporated under vacuum to leave a yellow oil. Flash chromatography through 150 g of silica gel (1:1 EtOAc/hexane) yielded 2.00 g (99%) of a colorless oil.

$^1$H-NMR (300 MHz, $CDCl_3$): δ 0.14 (s, 3H, $SiCH_3$), 0.28 S, 3H, $SiCH_3$), 0.95 (s, 9H, Sit-Bu), 0.95 (d, partially obscured, —$CHCH_3$), 1.08 (s, 9H, Sit-Bu), 2.05 (s, $CH_3CO_2$—), 2.10–2.25 (m, —$CHCH_3$),3.48 (dd, J=9.8, 5.8 Hz, —$CH_AOSi$), 3.65 (dd, J=9.8, 7.5 Hz, —$CH_BOSi$), 4.01 (dd, J=6.2, 3.8 Hz, H4), 4.21 (d, J=15.3 Hz, —$CH_AOAc$), 4.35 (d, J=15.3 Hz, —$CH_BOAc$), 5.49 (dd, J=6.2, 9.5 Hz, H3), 6.83 (brd, J=9 Hz, NH), 7.35–7.70 (m, 10H, $SiPh_2$).

IR ($CHCl_3$): 3430 (NH), 1750 (β-lactam), 1740 (acetate), 1695 cm$^{-1}$ (amide).

FAB-MS: m/e=597 (M+H).

EXAMPLE 4

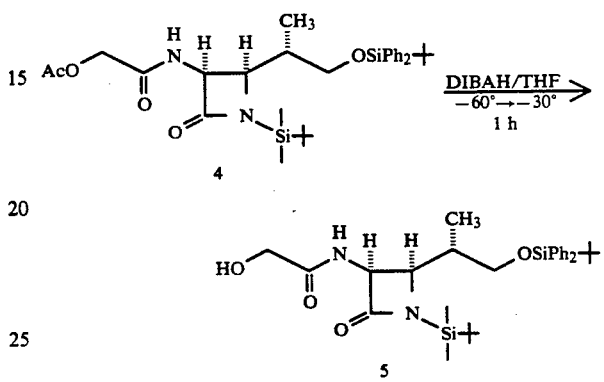

(±)-1-t-butyldimethylsilyl-4R-(1-t-butyldiphenyl-silyloxy-2S-propyl)-3S-hydroxyacetamido-azetidin-2-one (5)

A solution of azetidinone 4 (2.000 g, 3.356 mmol) in 25 ml of tetrahydrofuran was cooled to −60° C. and diisobutylaluminum hydride-hexane (1M, 13.4 ml) was added dropwise. The temperature was allowed to rise to −30° C. during 1 hour, and then the excess hydride was consumed by the addition of ethyl formate (1 ml). The reaction mixture was hydrolyzed with sat. sodium potassium tartrate, and after stirring vigorously for 1 hour, a clear two-phase mixture was obtained. Extractive work-up with ethyl acetate followed by drying ($MgSO_4$) and evaporation gave a yellow oil which was separated by flash chromatography through 150 g of silica gel (1:1 ethyl acetate/hexane) to yield 0.821 g (44%) of the title compound as colorless oil.

$^1$H-NMR (300 MHz, $CDCl_3$): δ 0.15 (s, 3H, $SiCH_3$), 0.32 (s, 3H, $SiCH_3$), 0.95 (d, partially obscured, —$CHCH_3$), 0.96 (s, 9H, Sit-Bu), 1.11 (s, 9H, Sit-Bu), 2.05–2.25 (m, —$CHCH_3$), 3.45–3.85 (m, 4H, —$CH_2OSi$, —$CH_2OH$), 3.98 (dd, J=6.0, 2.5 Hz, H4), 5.55 (dd, J=6.0, 10.0, H3), 7.3–7.7 (m, 10H, $SiPh_2$).

IR ($CHCl_3$): 3300–3450 (—OH, —NH), 1750 (β-lactam), 1685 cm$^{-1}$ (amide).

FAB-MS: m/e=555 (M+H).

EXAMPLE 5

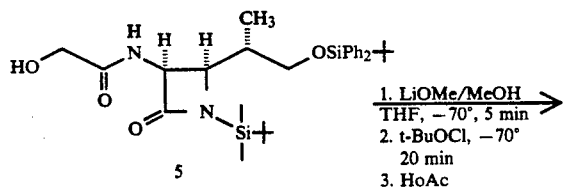

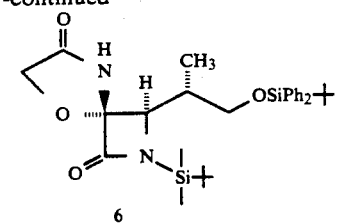

(±)-1-t-Butyldimethylsilyl-4R-(1-t-butyldiphenyl-silyloxy-2S-propyl)-3R-spiro[2-(1,3-oxazolidin-4-one)]-azetidin-2-one (6)

A solution of the azetidinone 5 (0.821 g, 1.48 mmol) in 15 ml of tetrahydrofuran was cooled to −70° C. and treated with a solution of lithium methoxide in tetrahydrofuran (freshly prepared by the addition of 2.4 ml of a 2.2M butyllithium/hexane to a solution of 0.9 ml of methanol in 11 ml of tetrahydrofuran). After 5 minutes, neat t-butyl hypochlorite (0.210 ml, 1.77 mmol) was added followed after an additional 15 minutes by glacial acetic acid (0.85 ml, 15 mmol). The reaction mixture was diluted with ethyl ether and washed with pH 7 phosphate buffer and brine. Drying (MgSO$_4$) and evaporation gave an oil which was purified by flash chromatography through 75 g of silica gel (3:7 EtOAc/hexane) to yield 0.662 g (81%) of the title compound as a colorless oil.

$^1$H-NMR (300 MHz CDCl$_3$): δ 0.077 (s, 3H, SiCH$_3$), 0.32 (s, 3H, SiCH$_3$), 0.92 (d, J=7.9 Hz, —CHCH$_3$), 0.97 (s, 9H, Sit-Bu), 1.08 (s, 9H, Sit-Bu), 2.25–2.40 (m, CHCH$_3$), 3.50–3.75 (m, —CH$_2$OSi), 4.03 (d, J=3.0 Hz, H4), 4.21 (d, J=13.5 Hz, —COCH$_A$O—), 4.39 (d, J=13.5 Hz, —COCH$_B$O—), 7.35–7.70 (m, 10H, SiPh$_2$).

IR (CHCl$_3$): 1755 (β-lactam), 1730 cm$^{-1}$ (oxazolidinone).

FAB-MS: m/e=553 (M+H).

EXAMPLE 6

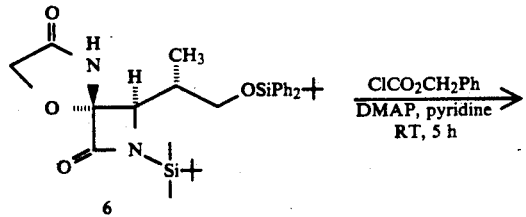

(±)-1-t-Butyldimethylsilyl-4R-(1-t-butyldiphenyl-silyloxy-2S-propyl)-3R-spiro[2-(3-benzyloxycarbonyl-1,3-oxazolidin-4-one)]-azetidin-2-one (7)

To a solution of the azetidinone 6 (0.250 g, 0.453 mmol) and 4-dimethylaminopyridine (0.277 g, 2.27 mmol) in 4.0 ml of pyridine was added benzyl chloroformate (0.323 ml, 2.27 mmol). A slight exotherm occurred and some gas was evolved. After 5 hours at room temperature, the reaction mixture was evaporated to dryness in vacuo. The residue was partitioned between ethyl ether and sat. NH$_4$Cl and the organic layer was washed with sat. NaHCO$_3$ and brine. Drying (MgSO$_4$), evaporation, and purification by flash chromatography through 25 g of silica gel (3:7 EtOAc/hexane) yielded 0.240 g (77%) of the title compound as a colorless oil.

$^1$H-NMR (300 MHz, CDCl$_3$): δ −0.038 (s, 3H, SiCH$_3$), 0.13 (s, 3H, SiCH$_3$), 0.83 (s, 9H, Sit-Bu), 0.84 (d, partially obscured, —CHCH$_3$), 1.07 (s, 9H, Sit-Bu), 1.95–2.10 (m, —CHCH$_3$), 3.37 (dd, J=9.8, 7.2 Hz, —CH$_A$OSi), 3.59 (dd, J=9.8, 5.2, —CH$_B$OSi), 3.74 (d, J=8.85 Hz, H4), 4.28 (d, J=14.5 Hz, —COCH$_A$O—), 4.43 (d, J=14.5 Hz, —COCH$_B$O—), 5.25–5.40 (AB, 2H, —OCH$_2$Ph), 7.3–7.7 (m, 15H, ArH).

IR (CHCl$_3$); 1805, 1750 (N-acyl-oxazolidinone), 1765 cm$^{-1}$ (β-lactam).

EXAMPLE 7

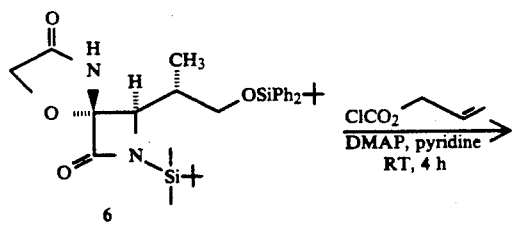

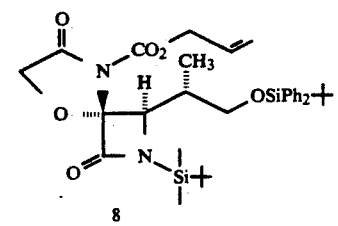

(±)-1-t-Butyldimethylsilyl-4R-(1-t-butyldiphenyl-silyloxy-2S-propyl)-3R-spiro[2-(3-allyloxycarbonyl-1,3-oxazolidin-4-one)]-azetidin-2-one (8)

In a manner analogous to that described in the previous example, except that allyl chloroformate was used instead of benzyl chloroformate, the azetidinone 6 (0.249 g, 0.451 mmol) gave the title compound (0.297 g, >100% crude yield) as a colorless oil.

$^1$H-NMR (300 MHz, CDCl$_3$): δ 0.034 (s, 3H, SiCH$_3$), 0.21 (s, 3H, SiCH$_3$), 0.90 (s, 9H, Sit-Bu), 0.99 (d, J=7.51 Hz, —CHCH$_3$), 1.13 (s, 9H, Sit-Bu), 2.10–2.25 (m, —CHCH$_3$), 3.47 (dd, J=9.9, 8.1 Hz, —CH$_A$OSi), 3.72 (dd, J=9.9, 4.2 Hz, —CH$_B$OSi), 3.81 (d, J=9.9 Hz, H4), 4.34 (d, J=15 Hz, —COCH$_A$O—), 4.49 (d, J=15 Hz, —COCH$_B$O), 4.75–4.90 (m, 2H, —OCH$_2$C=C), 5.30–5.55 (m, 2H, —C=CH$_2$), 5.90–6.05 (m, 1H, —CH=C), 7.40–7.75 (m, 10H, SiPh$_2$).

IR (CHCl$_3$): 1805, 1750 (N-acyl-oxazolidinone), 1765 cm$^{-1}$ (β-lactam).

EXAMPLE 8

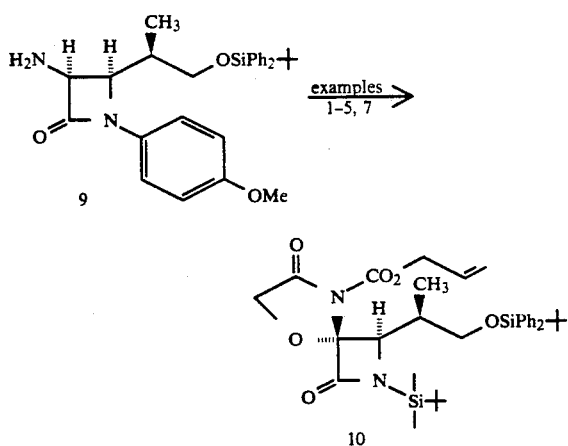

(±)-1-t-Butyldimethylsilyl-4R-(1-t-butyldiphenyl-silyloxy-2R-propyl)-3R-spiro[2-(3-allyloxycarbonyl-1,3-oxazolidin-4-one)]-azetidin-2-one (10)

In a manner analogous to that described in Examples 1–5 and 7, the title compound was prepared from amine 9.

$^1$H-NMR (300 MHz, CDCl$_3$): δ 0.26 (s, 3H, SiCH$_3$), 0.29 (s, 3H, SiCH$_3$), 1.02 (s, 9H, Si-t-Bu), 1.07 (s, 9H, Sit-Bu), 1.09 (d, partially obscured, —CHCH$_3$), 1.95–2.10 (m, —CHCH$_3$), 3.45–3.60 (m, 2H, —CH$_2$OSi), 3.93 (d, J=15.5 Hz, —COCH$_A$O—), 4.00 (d, J=8.8 Hz, H4), 4.29 (d, J=15.5, —COCH$_B$O—), 4.71 (d, J=5.4 Hz, —OCH$_2$C≡C), 5.20–5.45 (m, 2H, C=CH$_2$), 5.8–6.0 (m, 1H, —CH=C), 7.35–7.65 (m, 10H, SiPh$_2$).

EXAMPLE 9

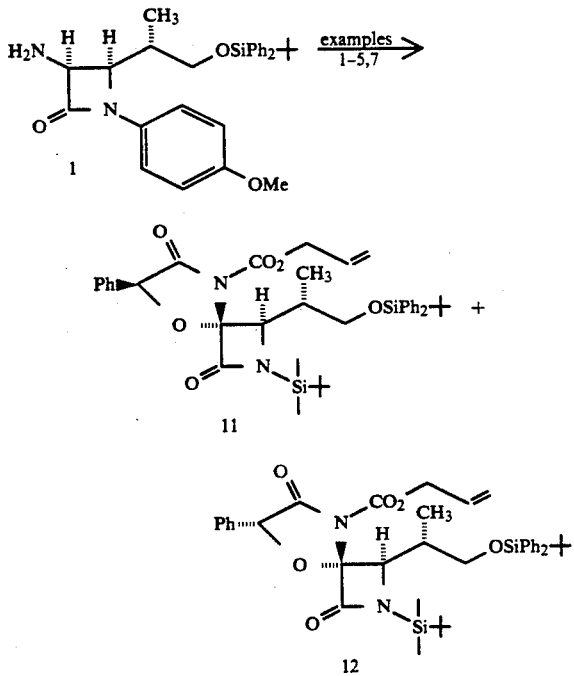

(±)-1-t-Butyldimethylsilyl-4R-(1-t-butyldiphenyl-silyloxy-2S-propyl)-3R-spiro[2-3-allyloxycarbonyl)-5S-phenyl-1,3-oxazolidin-4-one)]-azetidin-2-one (11) and
(±)-1-t-Butyldimethylsilyl-4R-(1-t-butyldiphenyl-silyloxy-2S-propyl)-3R-spiro[2-(3-allyloxycarbonyl-5R-phenyl-1,3-oxazolidin-4-one)]-azetidin-2-one (12)

In a manner analogous to that described in Examples 1–5 and 7, except that acetylmandelyl chloride was used in place of acetoxyacetyl chloride in Example 1, the chromatographically separable isomers 11 and 12 were prepared.

11
$^1$H-NMR (300 MHz, CDCl$_3$): δ 0.012 (s, 3H, SiCH$_3$), 0.20 (s, 3H, SiCH$_3$), 0.87 (s, 9H, Sit-Bu), 1.02 (d, J=6.47 Hz, —CHCH$_3$), 1.09 (s, 9H, Sit-Bu), 2.15–2.30 (m, —CHCH$_3$), 3.48 (dd, J=9.9, 7.2, —CH$_A$OSi), 3.74 (dd, J=9.9, 5.2 Hz, —CH$_B$OSi), 3.92 (d, J=9.95 Hz, H4), 4.70–4.85 (m, —OCH$_2$C=C), 5.25–5.50 (m, —CH=CH$_2$), 5.28 (s, —OCHPh), 5.85–6.00 (m, —CH=C), 7.35–7.70 (m, 15H, ArH).

IR (CHCl$_3$): 18.05, 1745 (N-acyl-oxazolidinone), 1765 cm$^{-1}$ (β-lactam).

12
$^1$H-NMR (300 MHz, CDCl$_3$): δ-0.048 (s, 3H, SiCH$_3$), 0.22 (s, 3H, SiCH$_3$), 0.85 (s, 9H, Sit-Bu), 0.87 (d, partially obscured, —CHCH$_3$), 1.08 (s, 9H, Sit-Bu), 2.15–2.25 (m, —CHCH$_3$), 3.42 (dd, J=9.9, 7.5 Hz, —CH$_A$OSi), 3.68 (dd, J=9.9, 3.1 Hz, —CH$_B$OSi), 3.89 (d, J=10.3 Hz, H4), 4.75–4.90 (m, —OCH$_2$C=C), 5.25–5.50 (m, —C=CH$_2$), 5.53 (s, —OCHPh), 5.85–6.00 (m, —CH=C), 7.30–7.65 (m, 15H, ArH).

IR (CHCl$_3$): 1805, 1750 (N-acyl-oxazolidinone), 1760 cm$^{-1}$ (β-lactam).

EXAMPLE 10

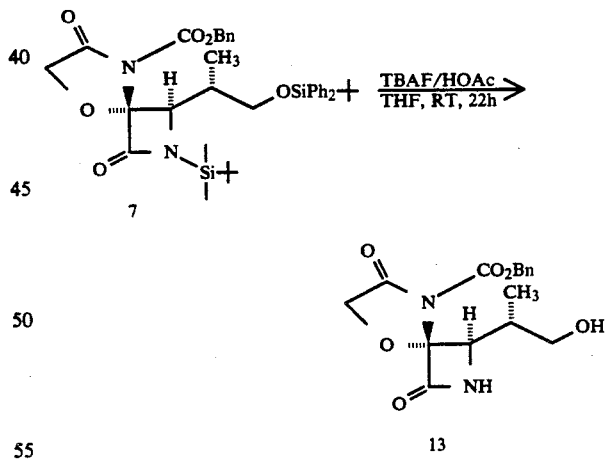

(±)-4R-(1-hydroxy-2S-propyl)-3R-spiro[2-(3-benzyloxycarbonyl-1,3-oxazolidion-4-one)]-azetidin-2-one (13)

To a solution of the azetidinone 7 (240 mg, 0.350 mmol) in 2 ml of tetrahydrofuran were added tetra-n-butylammonium fluoride (1.4 ml of a 1.0M solution in THF) and glacial acetic acid (0.25 ml, 4.3 mmol). After stirring at room temperature for 22 hours, the reaction mixture was evaporated in vacuo and the residue was separated by flash chromatography through 50 g of silica gel (EtOAc) to yield 81 mg (69%) of the title compound as a white solid which was contaminated with a small amount of a by-product resulting from acyl-transfer of the allyloxycarbonyl group from the oxazolidinone nitrogen to the hydroxyl. This minor impurity was removed in a subsequent step. $^1$H-NMR (300 MHz, CDCl$_3$): δ 0.75 (d, J=6.4 hz, —CH$_3$), 1.8–2.0 (m, —CHCH$_3$), 3.33 (dd, J=8.4, 10.5 Hz, —CH$_A$OH), 3.56 (dd, J=4.5, 10.5 Hz, —CH$_B$OH), 3.64 (d, J=11.2 Hz, H4), 4.30 (d, J=15.5 Hz, —COCH$_A$O—), 4.49 (d, J=15.5 Hz, —COCH$_B$O—), 5.31 (d, J=12.0 Hz, —OCH$_A$-Ph), 5.41 (d, J=12.0 Hz, —OCH$_B$-Ph), 6.64 (bs, —NH), 7.35–7.50 (m, 5H, PhH).

IR (CHCl$_3$): 3600–3200 (OH), 3440 (NH), 1805, 1740 (N-acyl-oxazolidinone), 1785 cm$^{-1}$ (β-lactam).

EXAMPLE 11

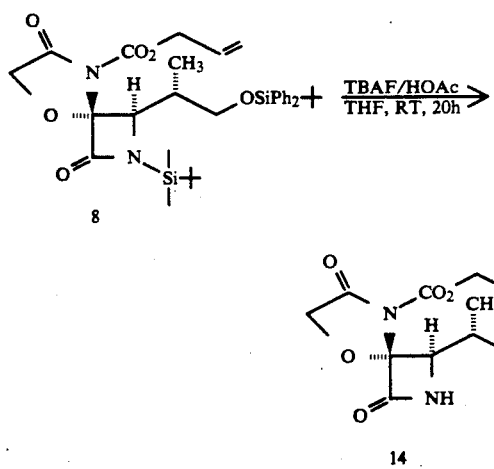

(±)-4R-(1-hydroxy-2S-propyl)-3R-spiro[2-(3-allyloxycarbonyl-1,3-oxazolidin-4-one)]-azetidin-2-one (14)

In a manner analogous to that described in Example 10, the azetidinone 8 (297 mg, 0.451 mmol) was desilylated to yield the title compound 14 (91.4 mg, 71%) as an oil. This product contained a minor amount (approx. 25%) of the carbonate resulting from transacylation of the allyloxycarbonyl group from the oxazolidinone to the hydroxyl. This minor isomer was removed in a subsequent step.

$^1$H-NMR (300 MHz, CDCl$_3$): δ 0.86 (d, J=6.4 Hz, CH$_3$), 1.95–2.15 (m, —CHCH$_3$), 3.35–3.70 (ABX, —CH$_2$OH), 3.71 (d, J=10.1 Hz, H4), 4.32 (d, J=14.4 Hz, —COCH$_A$O—), 4.49 (d, J=14.4 Hz, —COCH$_B$O—), 4.75–4.85 (m, —OCH$_2$C=C), 5.25–5.50 (m, =C=CH$_2$), 5.85–6.05 (m, —CH=C).

IR (CHCl$_3$): 3600–3200 (OH), 3440 (NH), 1800, 1740 (N-acyl-oxazolidinone), 1785 cm$^{-1}$ (β-lactam).

EXAMPLE 12

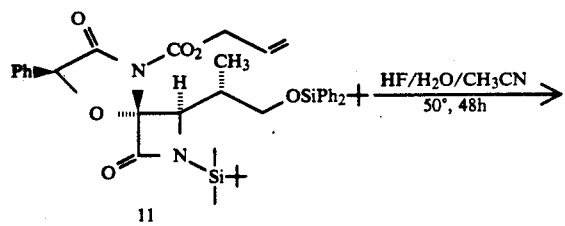

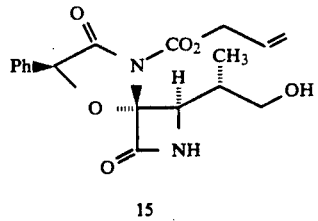

(±-4R-(1-hydroxy-2S-propyl)-3R-spiro[2-(3-allyloxycarbonyl-5S-phenyl-1,3-oxazolidin-4-one)]-azetidin-2-one (15)

To a solution of the silyl ether 11 (297 mg, 0.417 mmol) in 4 ml of acetonitrile was added 5N aqueous hydrofluoric acid (0.42 ml). The reaction mixture was heated at 50° C. for 48 hours and was then cooled to room temperature, diluted with ethyl acetate, and washed with sat. NaHCO$_3$ and brine. Drying (MgSO$_4$) and evaporation in vacuo yielded 210 mg (>100%) of crude 15 as a colorless oil which was used without purification.

$^1$H-NMR (300 MHz, CDCl$_3$): δ 0.94 (d, J=6.5 Hz, —CH$_3$), 2.10–2.25 (m, —CHCH$_3$), 3.46 (dd, J=8.7, 11.1 Hz, —CH$_A$OH), 3.74 (dd, J=4.4, 11.1 Hz, —CH$_B$OH), 3.84 (d, J=11.1 Hz, H4), 4.75–4.90 (m, —OCH$_2$C=C), 5.30 (s, —OCHPh), 5.25–5.50 (m, =C=CH$_2$), 5.85–6.00 (m, —CH=C), 7.35–7.55 (m, 5H, ArH).

EXAMPLE 13

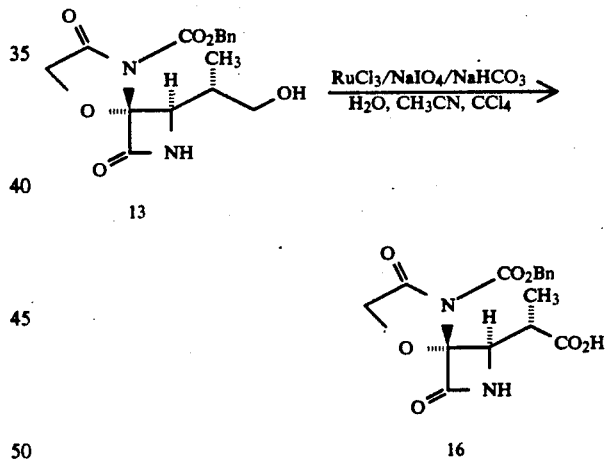

(±)-4R-(1S-carboxyethyl)-3R-spiro[2-(3-benzyloxycarbonyl-1,3-oxazolidin-4-one)]-azetidin-2-one (16)

To a solution of the alcohol 13 (81.0 mg, 0.243 mmol) in 1 ml of acetonitrile and 0.4 ml of water was added 1 ml of carbon tetrachloride followed by a solution of sodium metaperiodate (156 mg, 0.729 mmol) in 1 ml of water which had been adjusted to neutral pH with 1M aqueous sodium bicarbonate (0.15 ml), and finally a solution of ruthenium trichloride hydrate (3 mg, 0.01 mmol) in 0.1 ml of water. The two-phase reaction mixture was vigorously stirred at room temperature for 2 hours and was then partitioned between ethyl acetate-tetrahydrofuran (1:1) and brine. The organic phase was diluted with toluene and evaporated to dryness in vacuo. The dark residual solid was flash chromatographed through 5 g of silica gel (100:100:1

EtOAc/THF/HOAc) to yield 64.5 mg of the title compound as a tan solid which still contained the minor impurity which was introduced in the preceding step (Example 10). Further separation of a portion (28.5 mg) of the above product by preparative TLC on silica gel (150:50:1 EtOAc/THF/HOAc) gave 18.0 mg of pure 16 as a white solid.

$^1$H-NMR (300 MHz, d$_6$-acetone): δ 1.14 (d, J=7.2 Hz, —CH$_3$), 2.75-2.90 (m, —CHCH$_3$), 3.91 (d, J=10.2 Hz, H4), 4.45-4.60 (AB, —COCH$_2$O—), 5.39 (s, —OCH$_2$Ph), 7.3-7.6 (m, 5H, PhH).

EXAMPLE 14

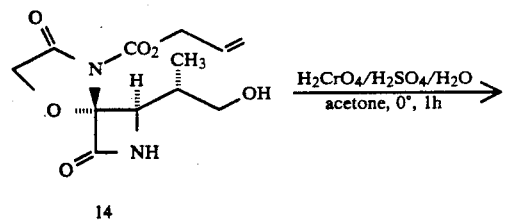

14

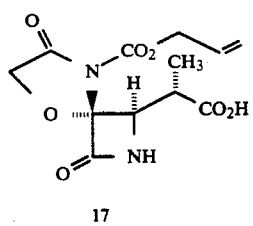

17

(±)-4R-(1S-carboxyethyl)-3R-spiro[2-(3-alloxycarbonyl-1,3-oxazolidin-4-one)]-azetidin-2-one (17)

To a solution of alcohol 14 (91.4 mg, 0.322 mmol) in 3 ml of acetone at 0° C. was added excess 2N Jones reagent (0.5 ml). The stirred reaction mixture was allowed to warm to room temperature during 1 hour, and then isopropanol (0.5 ml) was added to consume the excess oxidant. After several minutes a large excess of anhydrous sodium sulfate was added and the mixture was vigorously stirred and then filtered, washing the salts with ethyl acetate - tetrahydrofuran (3:1).Evaporation of the filtrate gave 118 mg of a green solid which was purified by flash chromatography through 2 g of silica gel (150:50:1 EtOAc/THF/HOAc) to yield 84.2 mg of the title compound as a white solid which still contained the minor impurity which was introduced in the preceding step (Example 11).

$^1$H-NMR (300 MHz, d$_6$-acetone): δ 1.20 (d, J=6.35 Hz, —CH$_3$), 2.8-3.0 (m,—CHCH$_3$), 3.93 (d, J=11.1 Hz, H4), 4.45-4.60 (AB, —COCH$_2$O—), 4.75-4.90 (m, —OCH$_2$C═C), 5.25-5.55 (m, —C═CH$_2$), 5.95-6.10 (m, —CH═C).

EXAMPLE 15

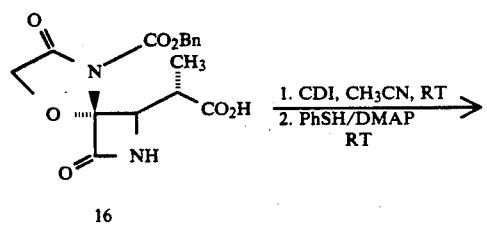

16

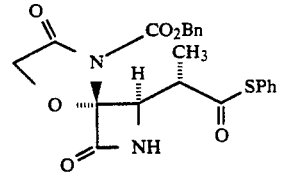

18

(±)-4R-[1S-(phenylthio)carbonylethyl]-3R-spiro[2-(3-benzyloxycarbonyl-1,3-oxazolidin-4-one)]-azetidin-2-one (18)

To a mixture of the carboxylic acid 16 (10.8 mg, 0.0310 mmol) in 0.35 ml of acetonitrile was added a solution of 1,1'-carbonyldiimidazole in acetonitrile (0.5M, 0.095 ml, 0.048 mmol). After stirring at room temperature for 30 minutes, the reaction mixture had become homogeneous and a solution of 4-dimethylaminopyridine in acetonitrile (0.10 M, 0.030 ml, 0.0030 mmol) was added followed by neat thiophenol (0.010 ml, 0.097 mmol). After 15 minutes, the reaction mixture was evaporated in vacuo, and the residue was separated by preparation TLC on silica gel (3:2 EtOAc/hexane) to yield 4.6 mg (34%) of the title compound as a white solid.

$^1$H-NMR (300 MHz, CDCl$_3$): δ 1.21 (d, J=7.15 Hz, —CH$_3$), 3.00-3.15 (m, —CHCH$_3$), 3.95 (d, J=11.2 Hz, H4), 4.33 (d, J=15.4 Hz, —COCH$_A$O—), 4.51 (d, J=15.4 Hz, —COCH$_B$O—), 5.41 (s, —OCH$_2$Ph), 7.30-7.55 (m, 10H, ArH).

IR (CHCl$_3$): 3430 (NH), 1800, 1740 (N-acyl-oxazolidinone), 1795 (β-lactam), 1690 cm$^{-1}$ (thioester).

EXAMPLE 16

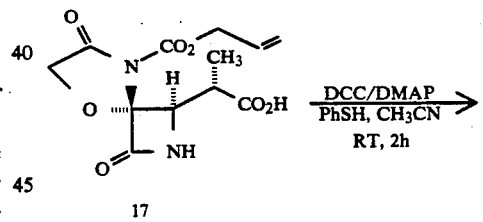

17

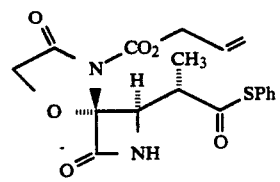

19

(±)-4R-[1S-(phenylthio)carbonylethyl]-3R-spiro[2-(3-allyloxycarbonyl-1,3-oxazolidin-4-one)]-azetidin-2-one (19)

To a solution of carboxylic acid 17 (14.1 mg, 0.0473 mmol) in 0.5 ml of acetonitrile were added a solution of 4-dimethylaminopyridine in acetonitrile (0.10M, 0.050 ml), neat thiophenol (0.00080 ml, 0.078 mmol), and a solution of 1,3-dicyclohexylcarbodiimide in acetonitrile (0.50M, 0.125 ml). After stirring at room temperature for 2 hours, the reaction mixture was filtered and evaporated to leave an oil which was separated by preparative TLC on silica gel (3:7 EtOAc/CH₂Cl₂) to yield 8.0 mg (43%) of the title thioester as a white solid.

¹H-NMR (300 MHz, CDCl₃): δ 1.32 (d, J=7.2 Hz, —CH₃), 3.20–3.35 (m, —CHCH₃), 3.99 (d, J=10.3 Hz, H4), 4.34 (d, J=15.4 Hz, —COCH$_A$O—), 4.51 (d, J=15.4 Hz, —COCH$_B$O—), 4.8–4.9 (m, —OCH₂C=C), 5.35–5.355 (m, —C=CH₂), 5.95–6.10 (m, —CH=C), 6.38 (Bs, NH, 7.35–7.50 (m, 5H, PhH).

IR (CHCl₃): 3430 (NH), 1800, 1740 (N-acyl-oxazolidinone), 1795 (β-lactam), 1695 cm⁻¹ (thioester).

EXAMPLES 17–22

Operating as described in the previous examples, the following compounds were analogously prepared:

EXAMPLE 23

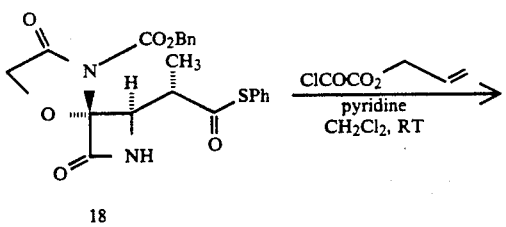

| | Ex. | ¹H-NMR (300 MHz, CDCl₃) | | |
|---|---|---|---|---|
| | | H4 | Ha | Hb |
| (structure) | 17 | δ 3.94, d  J=11.2Hz | 4.51, d  J=15.4 | 4.32, d  J=15.4 |
| (structure) | 18 | 3.99, d  J=10.2 | 4.51, d  J=15.4 | 4.33, d  J=15.4 |
| (structure) | 19. | 4.13, d  J=11.2 | — | 5.32, s |
| (structure) | 20 | 4.12, d  J=11.2 | — | 5.31, s |
| (structure) | 21 | 4.14, d  J=10.3 | 5.59, s | — |
| (structure) | 22 | 4.14, d  J=11.2 | 5.58, s | — |

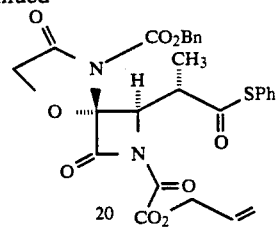

(±)-1-alloxalyl-4R-[1S-(phenylthio)carbonylethyl]-3R-spiro[2-(3-benzyloxycarbonyl-1,3-oxazolidin-4-one)]-azetidin-2-one (20)

To a solution of the thioester 18 (3.5 mg, 0.0080 mmol) in 0.35 ml of methylene chloride at room temperature was added pyridine (0.0030 ml, 0.037 mmol) followed by allyl oxalyl chloride (0.0040 ml, 0.032 mmol). The progress of the reaction was monitored by TLC on silica gel (2:3 EtOAc/hexane) and after 1.75 hours additional pyridine (0.0040 ml, 0.049 mmol) and allyl oxalyl chloride (0.0040 ml, 0.032 mmol) were added. After 5 hours more, the reaction was complete and the solution was diluted with ethyl ether and washed with pH 7 phosphate buffer and brine. Drying and evaporation gave 4.4 mg (100%) of the title compound as a white solid.

$^1$H-NMR (300 MHz, CDCl$_3$): δ 1.12 (d, J=7.2 Hz, —CH$_3$), 3.10–3.25 (m, —CHCH$_2$), 4.40–4.55 (AB, —COCH$_2$O—), 4.68 (d, J=9.7 Hz, H4), 4.8–4.9 (m, —OCH$_2$C=C), 5.3–5.5 (m, —C=CH$_2$), 5.44 (s, —OCH$_2$Ph), 5.90–6.05 (m, —CH=C) 7.40–7.55 (m, 10H, ArH).

IR (CHCl$_3$): 1825, 1790, 1760, 1745, 1720, 1696 cm$^{-1}$.

EXAMPLE 24

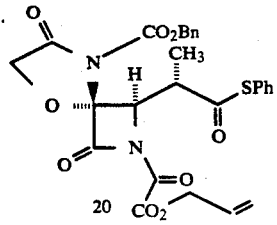

(±)-Allyl-(1S,5R)-1-methyl-2-phenylthio-6R-spiro[2-(3-benzyloxycarbonyl-1,3-oxazolidin-4-one)]-carbapen-2-em-3-carboxylate (21)

To a solution of the oxalimide 20 (4.4 mg, 0.0080 mmol) in 0.25 ml of toluene was added excess triethyl phosphite (0.050 ml, 0.29 mmol) and the reaction mixture was heated to 90° C. After 25 minutes, the solution was cooled to room temperature and evaporated under high vacuum to give 6.4 mg of a yellow oil. The crude phosphorane thus obtained was dissolved in p-xylene, a crystal of hydroquinone was added, and the solution was heated to reflux (138° C.). The progress of the cyclization was monitored by TLC on silica gel (1:1 EtOAc/hexane) and the reaction was judged to be complete after 1 hour. After cooling to room temperature, the solution was evaporated to leave a yellow oil. Separation by preparative TLC on silica gel (1:1 EtOAc/hexane) yielded 1.8 mg (43%) of the title carbapenem as a colorless oil.

$^1$H-NMR (300 MHz, CDCl$_3$): δ 0.92 (d, J=7.3 Hz, —CH$_3$), 3.35–3.45 (m, H1), 4.00 (d, J=7.7 Hz, H5), 4.36 (d, J=15.4 Hz, —COCH$_A$O—), 4.50 (d, J=15.4 Hz, —COCH$_B$O—), 4.7–4.9 (m, —OCH$_2$C=C), 5.25–5.55 (M,—C=CH$_2$), 5.42 (s, —OCH$_2$Ph), 5.95–6.05 (m, —CH=C), 7.15–7.50 (m, 10H, ArH).

IR (CHCl$_3$): 1795, 1740 cm$^{-1}$.

UV (CH$_3$CN): λmax=326 nm (ε=7,900).

EXAMPLES 25–30

Operating as described in the preceeding examples, the following compounds were analogously prepared:

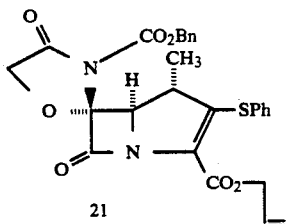

| Ex. | λmax (CH$_3$CN) |
|---|---|
| 25 | 319 nm (ε=8,000) |
| 26 | 325 nm (ε=9,600) |
| 27 | 318 nm (ε=7,700) |
| 28 | 326 nm (ε=10,600) |

| Ex. | | λmax (CH₃CN) |
|---|---|---|
| 29 | 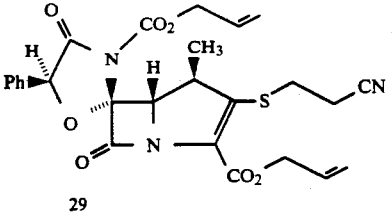 29 | 319 nm (ε=7,000) |
| 30 | 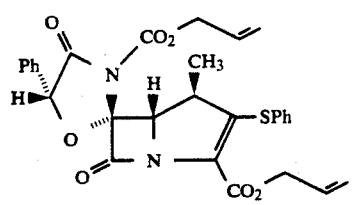 30 | 326 nm (ε=8,400) |

EXAMPLE 31

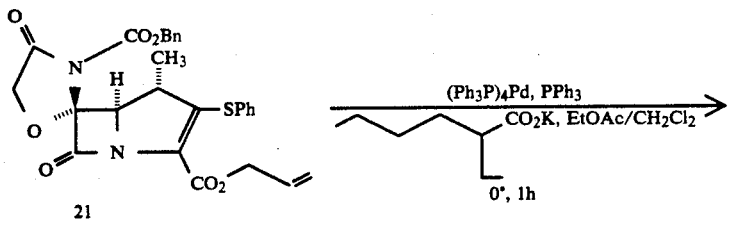

(±)-Potassium-(1S,5R)-1-methyl-2-phenylthio-6R-spiro[2-(3-benzyloxycarbonyl-1,3-oxazolidin-4-one)-carbapen-2-em-3-carboxylate (22)

To a solution of the carbapenem 21 (1.7 mg, 0.0033 mmol) in 1:1 ethyl acetate-methylene chloride (0.3 ml) at 0° C. were added in sequence a solution of triphenylphosphine in ethyl acetate (0.030M, 0.033 ml), a solution of potassium 2-ethylhexanoate in ethyl acetate (0.50M, 0.0080 ml), and a solution of tetrakis(triphenylphosphine)palladium in methylene chloride (0.010M, 0.033 ml). After 1 hour, the solution was evaporated and the residue was extracted with 3:1 water-tetrahydrofuran. The extract was separated by reverse-phase preparative TLC (3:1 H₂O/THF) to yield the title compound as a white lyophilized solid.

¹H-NMR (300 MHz, D₂O): δ 0.85 (d, J=7.3 Hz, —CH₃), 3.20–3.35 (m, H1), 4.12 (d, J=8.4 Hz, H5), 4.53 (s, —COCH₂O—), 5.35–5.55 (AB, —OCH₂Ph), 7.2–7.5 (m, 10H, ArH).

UV (H₂O): λmax=300 nm.

EXAMPLE 32

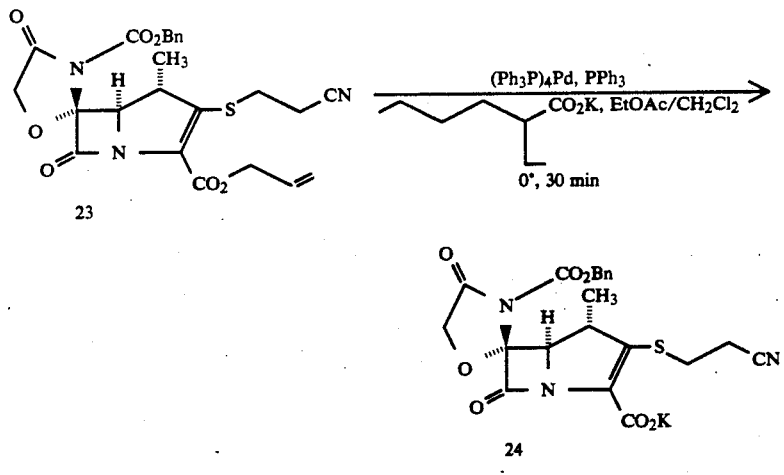

(±)-Potassium)-(1S,5R)-2-(2-cyanoethylthio)-1-methyl-6R-spiro[2-(3-benzyloxycarbonyl-1,3-oxazolidin-4-one)]-carbapen-2-em-3-carboxylate (24)

In a manner analogous to that described in Example 31, the carbapenem 23 (5.3 mg, 0.011 mmol) gave the

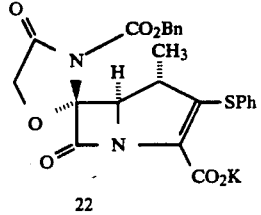

title compound (2.4 mg, 44%) as a white lyophilized solid.

$^1$H-NMR (300 MHz, D$_2$O): δ 1.33 (d, J=6.35 Hz, —CH$_3$), 2.65–3.05 (m, 4H, —SCH$_2$CH$_2$CN), 3.30–3.45 (m, H1), 4.25 (d, J=7.45 Hz, H5), 4.67 (s, —COCH$_2$O—), 5.35–5.55 (AB, —OCH$_2$Ph), 7.49 (bs, 5H, PhH).

EXAMPLE 33

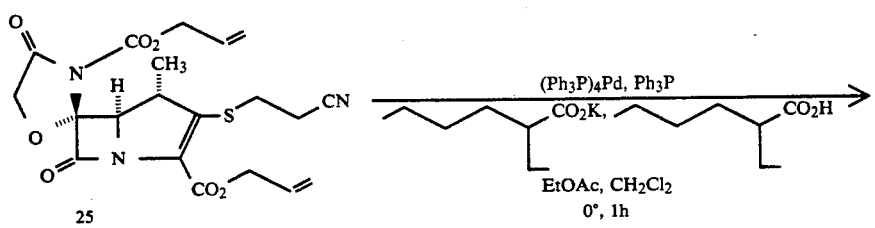

(±)-Potassium-(1S,5R)-2-(2-cyanoethylthio)-1-methyl-6R-spiro[2-(1,3-oxazolidin-4-one)]-carbapen-2-em-3-carboxylate (26)

To a solution of the carbapenem 25 in ethyl acetate-methylene chloride (1:1) at 0° C. is added triphenylphosphine (0.3 eq.), tetrakis(triphenylphosphine)palladium (0.1 eq.), potassium 2-ethylhexanoate (1.1 eq), and 2-ethylhexanoic acid (1.1 eq.). After 1 hour, isolation and purification as described in Example 31 gives the title compound.

EXAMPLE 34

In a manner analogous to that described in Example 33, the following compounds are also prepared:

from compound 27

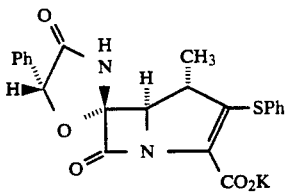

from compound 28

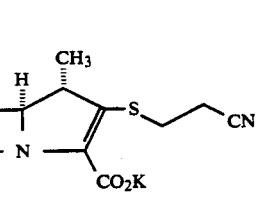

from compound 29

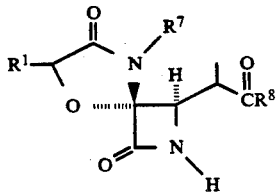

from compound 30

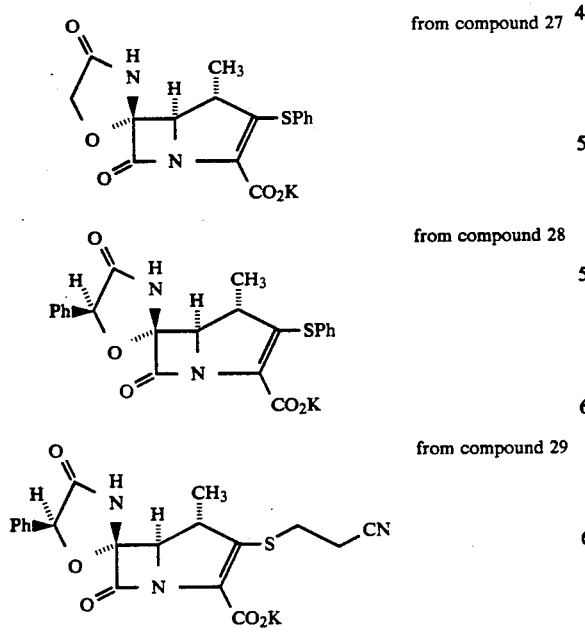

What is claimed is:

1. A compound of the structural formula:

wherein R$^1$ is hydrogen, C$_{1-8}$ alkyl or C$_{6-10}$ aryl; R$^7$ is hydrogen or a protecting group for amido nitrogen; and R$^8$ is hydroxy, hydrogen, C$_{1-8}$ alkylthio cyano-C$_2$alkylthio, C$_{6-10}$ arylthio, or 2-pyridylthio.

2. The compound of claim 1 wherein R$^1$ is hydrogen or phenyl.

3. The compound of claim 1 wherein R$^8$ is hydroxy, hydrogen, phenylthio, 2-(cyanoethyl)thio, or 2-pyridylthio.

4. The compound of claim 1 wherein R$^7$ is hydrogen or a carbamate protecting group for amido nitrogen.

5. The compound of claim 1 selected from the group consisting of
4R-(1S-carboxyethyl)-3R-spiro[2-(3-alloxycarbonyl-1,3-oxazolidin-4-one)]-azetidin-2-one (17),
4R-(1S-carboxyethyl)-3R-spiro[2-(3-benzyloxycarbonyl-1,3-oxazolidin-4-one)]-azetidin-2-one (16),
4R-[1S-(phenylthio)carbonylethyl]-3R-spiro[2-(3-benzyloxycarbonyl-1,3-oxazolidin-4-one)]-azetidin-2-one (18),
4R-[1S-(phenylthio)carbonylethyl]-3R-spiro[2-(3-allyloxycarbonyl-1,3-oxazolidin-4-one)]-azetidin-2-one (19),

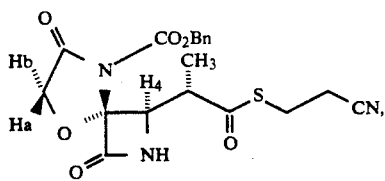

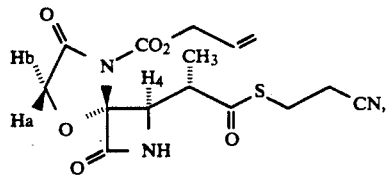

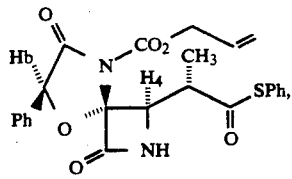

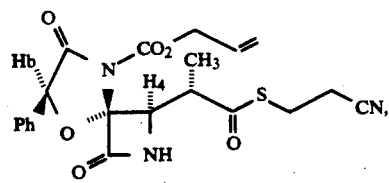

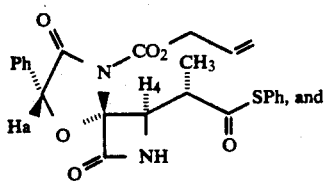

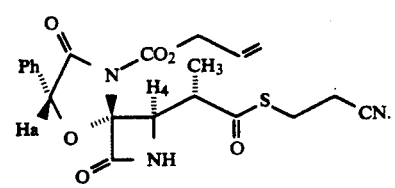

6. A compound of the structural formula:

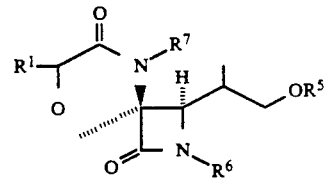

where $R^5$ is hydrogen or a protecting group for alcohol; $R^6$ is hydrogen or a protecting group for amido nitrogen; $R^7$ is hydrogen or a protecting group for amido nitrogen; and $R^1$ is hydrogen, $C_{1-8}$ alkyl, or $C_{6-10}$ aryl; with the condition that $R^6$ and $R^7$ as protecting groups are separately cleavable.

7. The compound of claim 6 wherein $R_1$ is hydrogen or phenyl.

8. The compound of claim 6 wherein $R^6$ is a protecting group for amido selected from silyl hydrocarbons where at least one of the three hydrocarbon substituents has four or more carbon atoms.

9. The compound of claim 6 wherein $R^5$ is selected from the group consisting of t-butyldiphenylsilyl, t-butyldimethylsilyl, benzyl, p-methoxybenzyl, methoxymethyl and benzyloxycarbonyl.

10. The compound of claim 6 wherein $R^7$ is a hydrogen or a carbamate protecting group for amido nitrogen.

11. The compound of claim 6 selected from the group consisting of 1-t-Butyldimethylsilyl-4R-(1-t-butyldiphenylsilyloxy-2S-propyl)-3R-spiro[2-(1,3-oxazolidin-4-one)]-azetidine-2-one (6), 1-t-Butyldimethylsilyl-4R-(1-t-butyldiphenylsilyloxy-2S-propyl)-3R-spiro[2-(3-benzyloxycarbonyl-1,3-oxazolidin-4-one)]-azetidin-2-one (7), 1-t-Butyldimethylsilyl-4R-(1-t-butyldiphenylsilyloxy-2S-propyl)-3R-spiro[2-(3-allyloxycarbonyl-1,3-oxazolidin-4-one)]-azetidin-2-one (8), 1-t-Butyldimethylsilyl-4R-(1-t-butyldiphenylsilyloxy-2R-propyl)-3R-spiro[2-(3-allyloxycarbonyl-1,3-oxazolidin-4-one)]-azetidin-2-one (10), 1-t-Butyldimethylsilyl-4R-(1-t-butyldiphenylsilyloxy-2S-propyl)-3R-spiro[2-(3-allyloxycarbonyl-5S-phenyl-1,3-oxazolidin-4-one)]-azetidin-2-one (11), 1-t-Butyldimethylsilyl-4R-(1-t-butyldiphenylsilyloxy-2S-propyl)-3R-spiro[2-(3-allyloxycarbonyl-5R-phenyl-1,3-oxazolidin-4-one)]-azetidine-2-one (12), 4R-(1-hydroxy-2S-propyl)-3R-spiro[2-(3-benzyloxycarbonyl-1,3-oxazolidon-4-one)]-azetidin-2-one (13), 4R-(1-hydroxy-2S-propyl)-3R-spiro[2-(3-allyloxycarbonyl-1,3-oxazolidin-4-one)]-azetidin-2-one (14), 4R-(1-hydroxy-2S-propyl)-3R-spiro[2-(3-allyloxycarbonyl-5S-phenyl-1,3-oxazolidin-4-one)]-azetidin-2-one (15).

* * * * *